United States Patent [19]

Canavesi et al.

[11] 4,323,716
[45] Apr. 6, 1982

[54] PROCESS AND CATALYST FOR THE PRODUCTION OF DICHLOROETHANE

[75] Inventors: Roberto Canavesi, Bollate; Ferdinando Ligorati, Usmate; Giancarlo Aglietti, Milan, all of Italy

[73] Assignee: Societa' Italiana Resine S.I.R. S.p.A., Milan, Italy

[21] Appl. No.: 113,553

[22] Filed: Jan. 21, 1980

Related U.S. Application Data

[63] Continuation of Ser. No. 617,951, Sep. 29, 1975, abandoned.

[30] Foreign Application Priority Data

Oct. 4, 1974 [IT] Italy ............................ 28051 A/74

[51] Int. Cl.$^3$ ............................................. C07C 17/02
[52] U.S. Cl. ................................... 570/243; 252/441; 570/245
[58] Field of Search .................. 252/441; 260/655 A; 570/243, 245

[56] References Cited

U.S. PATENT DOCUMENTS

| | | | |
|---|---|---|---|
| 3,433,581 | 3/1961 | Stephens et al. | 423/213.2 |
| 3,461,084 | 8/1969 | Li | 252/441 |
| 3,598,758 | 8/1971 | Koyanagi et al. | 252/429 |
| 3,634,330 | 1/1972 | Michel et al. | 252/441 |

*Primary Examiner*—Robert V. Hines
*Attorney, Agent, or Firm*—Christie, Parker & Hale

[57] ABSTRACT

An oxychlorination catalyst active in the production of dichloroethane from ethylene, hydrogen chloride and oxygen, consisting of copper chloride on a granular support consisting of alumina in the crystallographic form eta, having a total volume of pores of from 0.3 to 0.5 ml/g and a surface area of from 250 to 400 m$^2$/g with at least 90% of said volume attributable to pores with a radius of less than 40 Å and at least 90% of said surface area attributable to pores with a radius of less than 30 Å.

9 Claims, No Drawings

PROCESS AND CATALYST FOR THE PRODUCTION OF DICHLOROETHANE

This is a continuation of application Ser. No. 617,951, filed Sept. 29, 1975, and now abandoned.

This invention relates to the production of dichloroethane by oxychlorination of ethylene.

In particular, the invention concerns a process for the production of dichloroethane by contacting a gaseous flow containing ethylene, hydrogen chloride and oxygen, with a fluidized oxychlorination catalyst, consisting of supported copper chloride, obtained by depositing cupric chloride on a granular support, the said support consisting of alumina in the crystallographic form eta ($\eta$), having a total volume of pores of from 0.3 to 0.5 ml/g and a surface area of from 250 to 400 m$^2$/g, at least 90% of the said volume being attributable to pores with a radius of less than 40 Å, at least 90% of the said area being attributable to pores with a radius of less than 30 Å.

The invention provides a supported copper chloride catalyst, which is active in the production of dichloroethane from ethylene, hydrogen chloride and oxygen, the said catalyst being obtained by contacting a granular support with cupric chloride dissolved in a solvent and evaporating the said solvent, the said support consisting of alumina of crystallographic form eta, having a total volume of pores of from 0.3 to 0.5 ml/g and a surface area of from 250 and 400 m$^2$/g, at least 90%, of the said volume being attributable to pores with a radius of less than 40 Å, and at least 90% of the said area being attributable to pores with a radius of less than 30 Å.

Oxychlorination catalysts consisting of copper chloride or different types of solid supports are already known in the art. The catalyst in accordance with this invention may be distinguished from those of the prior art by the crystallographic form and the morphological characteristics of the alumina support, said features proving essential in view of the activity and selectivity of said catalyst shown in the process of the invention.

In particular, a suitable support for the catalyst of this invention consists of alumina in the form of granules with dimensions of from 20 to 100 microns, with a bulk density of about 1.10–1.15 g/cm$^3$, in the crystallographic form eta and having the morphological characteristics previously indicated.

Eta-alumina, which may be obtained, for example, by heating in air of bayerite (beta-Al$_2$O$_3$.3H$_2$O) at a temperature of from 250° to 500° C., crystallizes, as is known, in the cubic system (spinel).

Furthermore, it is desirable that the alumina should be devoid or substantially devoid of silica and of iron (silica content less than 0.01% and iron content less than 0.02% by weight), and it is preferable that the sodium content be maintained at values below 0.3% by weight.

The volume of the pores and the surface area of the alumina are critical, as is the distribution of these pores, and these values should fall within the ranges indicated above.

The best results are obtained when the alumina has a total volume of pores of 0.4 ml/g with at least 90% of the said volume attributable to pores with a radius of less than 30 Å, and a surface area of approximately 350 m$^2$/g, with at least 90% of the said area attributable to pores with a radius of less than 20 Å, these determinations being made according to the known B.E.T. method by absorption of nitrogen, at liquid nitrogen temperature ($-195°$ C.).

Preferably, the catalyst of this invention contains copper chloride in an amount corresponding to a content in copper (see metal) in the catalyst of from 2% to 8% by weight.

The best results are obtained with a content in copper (again, as metal) of 4–5% by weight in the catalyst.

In fact, no appreciable advantages are obtained with a copper content greater than 8% by weight: on the other hand, copper contents below 2% by weight require longer periods of contact under ethylene oxychlorination conditions.

The catalyst of this invention can be prepared in accordance with the conventional methods, the granular support being placed in contact with an aqueous and/or alcohol solution (for example, methanol) of cupric chloride.

To this end, anhydrous cupric chloride or dihydrate cupric chloride may be used, and in each case it is preferable to use a salt as pure as possible. Thus, for example, it is convenient to use salts having a content in cations other than copper (as for example iron) below at least 2% and in anions other than chlorine (such as nitrates) below 0.5%.

The said cupric chloride can be dissolved in the solvent up to a concentration of approximately 15% by weight and the granular support is then impregnated, operating at a temperature of from ambient temperature (20°–25° C.) to 70° C. The impregnated support is then dried at temperatures up to 200° C.

According to another known procedure, impregnation of the support and drying take place simultaneously by spraying the solution of cupric chloride on a fluidized bed of particles of the support, operating at a temperature of the order of 130° C.

The catalyst thus obtained has the desired characteristic relating to the non-volatility of the copper salt under the temperature conditions suitable for the ethylene oxychlorination.

It is therefore not necessary to add to the catalyst an alkali metal chloride, which is normally used in the prior art in order to reduce the volatility of the cupric chloride.

Therefore, in the preferred embodiment, the catalyst of this invention is devoid of alkali metal chloride, which, besides, affords no improvement to the characteristics of activity and selectivity shown by the catalyst under the oxychlorination conditions.

It is however possible, though not convenient, to add the said alkali metal chloride in an amount corresponding to a content in alkali metal of from 0.5% to 4.5% by weight in the catalyst.

In the latter case, the alkali metal chloride (preferably potassium chloride) may be dissolved in the same solution which contains the cupric chloride and then applied to the support in accordance with the procedures described above.

It is, however, preferable to dissolve the alkali metal chloride in water, apply the solution thus obtained to the fluidized support and apply then the aqueous solution of copper chloride.

In accordance with this invention, dichloroethane is prepared by supplying a gaseous flow containing ethylene, hydrogen chloride and oxygen to the fluidized catalyst.

In particular, it is convenient to use air as the source of oxygen and supply from 1.5 to 2.5 moles of hydrogen chloride and from 0.5 to 1.0 moles of oxygen, for each mole of ethylene. Optimum results are obtained with hydrogen chloride: ethylene: oxygen molar ratios of 2:1.055:0.8.

Furthermore, the oxychlorination operation is carried out at a temperature of from 200° to 240° C. and preferably from 215° to 230° C., and at a pressure of from 3 to 5 atms.

Moreover, the residence time of the gaseous flow, measured under the temperature and pressure conditions of oxychlorination and with the reactor devoid of catalyst, is generally of from 20 to 30 seconds.

The best results are obtained with residence times of the order of 27–30 seconds.

By preparing dichloroethane by means of the catalyst of this invention and in the conditions described above, conversions of at least 99% in moles with respect to the feed in ethylene and of at least 98% in moles with respect to the feed in hydrogen chloride can be achieved, while maintaining high selectivity values in dichloroethane.

It is considered that these especially favourable results are essentially attributable to the choice of the support for the catalyst of this invention.

It is to be noted that cupric chloride is an oxychlorination catalyst normally used in the preparation of dichloroethane from ethylene, hydrogen chloride and oxygen according to an overall reaction which may be represented by the following equation:

$$C_2H_4 + 2HCl + \tfrac{1}{2}O_2 \rightarrow C_2H_4Cl_2 + H_2O$$

Furthermore, according to what is known in the literature, the mechanism which leads to the formation of dichloroethane is represented by the equations given below, the main justification for these equations being based on the fact that cupric chloride decomposes on heating with generation of chlorine. In each case the proposed mechanism is the following:

$$2CuCl_2 + C_2H_4 \rightarrow C_2H_4Cl_2 + Cu_2Cl_2$$

$$Cu_2Cl_2 + \tfrac{1}{2}O_2 \rightarrow CuO \cdot CuCl_2$$

$$CuO \cdot CuCl_2 + HCl \rightarrow 2CuCl_2 + H_2O$$

and therefore the total reaction turns out to be that indicated earlier above.

However, it has been observed experimentally that when cupric chloride deposited on alumina is submitted to heating, at oxychlorination temperature, hydrogen chloride, rather than chlorine, is evolved.

In oxychlorination of ethylene, besides the principal reaction of formation of dichloroethane, secondary reactions also take place (collateral or consecutive to the principal reaction) which lead to the formation of by-products, especially compounds with a higher chlorination degree than dichloroethane and total oxidation compounds (carbon oxides).

It has been observed experimentally that alumina influences these secondary reactions.

Thus, for example, if a gaseous flow of dichloroethane is supplied to a fluidized bed of alumina particles, operating at oxychlorination temperatures, the said dichloroethane is partially transformed with formation of hydrogen chloride and of more highly chlorinated products.

Furthermore, if a little oxygen is added to the said gaseous flow of dichloroethane, there occurs, still in the same temperature conditions, combustion phenomena, whereas these combustion phenomena are absent when ethylene is supplied in place of dichloroethane.

Again, it has been noted that the phenomena of formation of secondary products are linked to the crystallographic form of the alumina, as well as to the surface characteristics of the alumina itself.

The influence of the alumina support on the activity and selectivity characteristics of the catalyst, and perhaps also on the mechanism of the oxychlorination reaction, is therefore quite clear.

In each case the phenomena of interaction between the copper salt and the support, probably linked with the acidity of the hydroxide groups of the alumina, are certainly relevant.

It therefore becomes clear that what is important is not so much the choice of alumina as a support, but rather that of the sum of characteristics shown by said alumina. Thus, the alumina of this invention, of crystallographic form eta and having a volume of pores, a surface area and a pore distribution within the ranges of values previously indicated, allows better results to be achieved in the production of dichloroethane by oxychlorination of ethylene, as will become clear from the following experimental examples.

EXAMPLE 1

For the preparation of the catalyst, eta alumina is used in granules of from 20 to 100 microns, and with a bulk density of 1.13 g/cm³.

The alumina has a total volume of pores equal to 0.4 ml/g, 25% of this volume is accounted for by pores with a radius of less than 12 Å and 95% of said volume is accounted for by pores with a radius of less than 30 Å, as results from B.E.T. determinations.

Furthermore, the alumina has a surface area of 362 m²/g, 25% of said area being accounted for by pores with a radius of less than 11 Å and 90% of said area being accounted for by pores with a radius of less than 21 Å.

89.5 parts by weight of the said alumina, which has been dried at 105° C., are placed in a tubular reactor, equipped with a porous plate at the bottom and with a heating jacket.

A flow of air is sent to the bottom of the reactor so as to ensure fluidification with a linear speed of gas of 4–8 cm/sec in operating conditions, and heat is supplied so as to bring the temperature of the fluid bed to 130° C.

Moreover, 10.6 parts by weight of copper chloride dihydrate are dissolved in water until a solution at 15% by weight of salt is formed, and the solution thus obtained is sprayed on the fluid bed, regulating the feed rate of the solution so as not to change the temperature of the bed to values below 120° C.

Throughout the whole operation of spraying the copper chloride solution, particular care is taken to keep the temperature in the fluid bed uniform and to avoid the formation of lumps.

Finally, the catalyst is cooled and discharged.

EXAMPLE 2

(comparison)

Approximately 2800 g of the catalyst, which has been prepared as described in Example 1, are placed in a tubular reactor having an internal diameter of 40 mm.

The reactor is fed at its bottom with a gaseous flow consisting of hydrogen chloride, ethylene and air in which the molar ratios of hydrogen chloride: ethylene: oxygen are of 2:1.055:0.8.

The supply is regulated in such a way as to ensure a linear velocity of gas equal to 9 cm/sec., when the said velocity is calculated on the empty tube, at the temperature and pressure indicated below.

Moreover, the reaction is carried out with the fluidized catalyst, at a temperature of 215° C., at a pressure of 1 atm. and with a residence time of 27-30 seconds.

The gases coming out at the top of the reactor are analysed and for each reagent the percentage of conversion, as well as the selectivity, is determined. The selectivity is expressed as the percentage of moles converted, which has reacted to give dichloroethane.

The following results have been obtained:

|  | hydrogen chloride | ethylene | oxygen |
| --- | --- | --- | --- |
| conversion | 97.5% | 100% | 95.5% |
| selectivity | 99.0% | 87% | 56.5% |

EXAMPLE 3

(comparison)

Operation is as in Example 2 with the sole difference that the temperature is maintained at 230° C.
The following results have been obtained:

|  | hydrogen chloride | ethylene | oxygen |
| --- | --- | --- | --- |
| conversion | 83.5% | 99.8% | 96% |
| selectivity | 98.0% | 84.0% | 53.0% |

EXAMPLE 4

Operation is as in Example 2 with the sole difference that the pressure is brought to 4 atms.
The following results have been obtained:

|  | hydrogen chloride | ethylene | oxygen |
| --- | --- | --- | --- |
| conversion | 98% | 99% | 70% |
| selectivity | 99.5% | 97% | 88% |

EXAMPLE 5

Operation is as in Example 4 with the sole difference that the temperature is brought to 230° C.
The following results have been obtained:

|  | hydrogen chloride | ethylene | oxygen |
| --- | --- | --- | --- |
| conversion | 98% | 99.7% | 84% |
| selectivity | 99% | 93% | 73% |

EXAMPLE 6

(comparison)

A catalyst is prepared following the procedure of Example 1, using an eta alumina support in granules of from 20 to 100 microns.

The said alumina has a total volume of pores of 0.33 ml/g and a surface area of 144 m$^2$/g.

It results from the B.E.T. determinations, moreover, that 25% of the volume of pores is accounted for by pores with a radius of less than 24 Å and 90% by pores with a radius of less than 250 Å.

Furthermore, 25% of the surface area is accounted for by pores with a radius of less than 22 Å and 90% by pores with a radius of less than 43 Å.

EXAMPLE 7

(comparison)

Dichloroethane is prepared operating with the catalyst of Example 6 and under the operative conditions of Example 2.
The following results have been obtained:

|  | hydrogen chloride | ethylene | oxygen |
| --- | --- | --- | --- |
| conversion | 95% | 97% | 96% |
| selectivity | 97.5% | 84% | 52% |

EXAMPLE 8

(comparison)

Dichloroethane is prepared operating with the catalyst of Example 6 and under the operative conditions of Example 4.
The following results have been obtained:

|  | hydrogen chloride | ethylene | oxygen |
| --- | --- | --- | --- |
| conversion | 97% | 98% | 82% |
| selectivity | 98% | 86% | 73.5% |

EXAMPLE 9

(comparison)

A catalyst is prepared following the procedure of Example 1, using an alumina of crystallographic form gamma in granules of from 25 to 90 microns and with a bulk density of 1.1.

Moreover, the said alumina has a total volume of pores equal 0.35 ml/g and a surface area of 180 m$^2$/g.

The said catalyst is used to prepare dichloroethane under the operative conditions of Example 2.
The following results have been obtained:

|  | hydrogen chloride | ethylene | oxygen |
| --- | --- | --- | --- |
| conversion | 90% | 94% | 97.5% |
| selectivity | 90% | 78% | 58% |

EXAMPLE 10

(comparison)

A catalyst is prepared according to the procedure of Example 1, using an alumina of crystallographic form gamma and alpha, with a total volume of pores of 0.18 ml/g and a surface area of 40 m$^2$/g.

The said alumina is in the form of granules of from 20 to 100 microns, and has a bulk density of 1.10-1.15 g/cm$^3$.

Preparing dichloroethane by means of this catalyst under the operative conditions of Example 9, activity and selectivity values similar to those reported in Example 9 are obtained.

EXAMPLE 11

(comparison)

A catalyst is prepared according to the procedure of Example 1, using as a support alumina of crystallographic form alpha having a surface area of 35 m²/g, and a volume of pores of 0.15 ml/g.

The said alumina is in the form of granules of from 20 to 100 microns.

The catalyst thus obtained shows practically no activity in the production of dichloroethane under the operative conditions of Example 10.

What we claim is:

1. An oxychlorination catalyst, active in the production of dichloroethane, from ethylene, hydrogen chloride and oxygen, consisting of supported copper chloride obtained by contacting a granular support with cupric chloride dissolved in a solvent and evaporating said solvent, the said support consisting of alumina in the crystallographic form eta, having a total volume of pores of from 0.3 to 0.5 ml/g and a surface area of from 250 to 400 m²/g with a least 90% of said volume attributable to pores with a radius of less than 40 Å and with at least 90% of said surface area attributable to pores with a radius of less than 30 Å.

2. The oxychlorination catalyst of claim 1, wherein said volume of pores is of 0.4 ml/g and said surface area is of approximately 350 m²/g, at least 90% of said volume being attributable to pores with a radius of less than 30 Å and at least 90% of said surface area being attributable to pores with a radius of less than 20 Å.

3. The oxychlorination catalyst of claim 1, wherein said granular support is in the form of granules of from 20 to 100 microns in size.

4. The oxychlorination catalyst of claim 1, wherein the content in copper calculated as metal is from 2 to 8% by weight.

5. A process for the production of dichloroethane, which comprises contacting a gaseous flow comprising ethylene, hydrogen chloride and oxygen at a temperature of from 200° to 240° C. and at a pressure of from 3 to 5 atmospheres with a fluidized catalyst consisting of supported copper chloride obtained by contacting a granular support with cupric chloride dissolved in a solvent and evaporating said solvent, said support consisting of alumina in the crystallographic form eta, having a total volume of pores of from 0.3 to 0.5 ml/g with at least 90% of said volume attributable to pores with a radius of less than 40 Å and a surface area of from 250 to 400 m²/g with at least 90% of said surface area attributable to pores with a radius of less than 30 Å.

6. The process of claim 5, wherein said gaseous flow comprises from 1.5 to 2.5 moles of hydrogen chloride and from 0.5 to 1.0 moles of oxygen for each mole of ethylene and the residence time of said gaseous flow under reaction conditions is from 20 to 30 seconds.

7. The process of claim 5, wherein said volume of pores is of 0.4 ml/g and said surface area is of approximately 350 m²/g, at least 90% of said volume being attributable to pores with a radius of less than 30 Å and at least 90% of said surface area being attributable to pores with a radius of less than 20 Å.

8. The process of claim 5, wherein said granular support is in the form of granules of from 20 to 100 microns in size.

9. The process of claim 5, wherein said catalyst contains from 2 to 8% by weight of copper calculated as metal.

* * * * *